United States Patent [19]

Dakka et al.

[11] Patent Number: 6,107,525
[45] Date of Patent: Aug. 22, 2000

[54] PROCESS FOR THE MANUFACTURE OF HYDROXYCARBONYL COMPOUNDS

[75] Inventors: Jihad Mohammed Dakka, Leuven; Georges Marie Karel Mathys, Bierbeek; Hans Karel Theresia Goris, Laakdal, all of Belgium

[73] Assignee: Exxon Chemical Patents Inc., Houston, Tex.

[21] Appl. No.: 09/171,830

[22] PCT Filed: Apr. 23, 1997

[86] PCT No.: PCT/EP97/02125

§ 371 Date: Oct. 26, 1998

§ 102(e) Date: Oct. 26, 1998

[87] PCT Pub. No.: WO97/41087

PCT Pub. Date: Nov. 6, 1997

[30] Foreign Application Priority Data

Apr. 26, 1996 [EP] European Pat. Off. .............. 96302982

[51] Int. Cl.$^7$ ..................................... C07C 45/27
[52] U.S. Cl. .......................... 568/485; 568/489; 568/591; 562/589
[58] Field of Search ..................... 568/384, 434, 568/449, 469.9, 485, 489, 591; 562/589

[56] References Cited

U.S. PATENT DOCUMENTS

| | | | |
|---|---|---|---|
| 5,025,101 | 6/1991 | Gorun et al. | 556/50 |
| 5,504,266 | 4/1996 | Tirtowidjojo et al. | 570/234 |

FOREIGN PATENT DOCUMENTS

| | | | |
|---|---|---|---|
| 1003840 | 6/1992 | Belgium . | |
| 0100118 | 2/1984 | European Pat. Off. | C07C 43/13 |

OTHER PUBLICATIONS

Synthesis, Aug. 1977, pp. 578–579, A. A. Frimer: "Synthesis of Alpha–Hydroxyacetals".

Cat. Rev. Sci. Eng. (1995) 37(2), 311 to 352 "Heteropoly Acids and Related Compounds as Catalysts for Fine Chemical Synthesis".

A. Wohl, Berichte, 1908, 3599 at 3609, "Zur Kenntnis der Dreikohlenstoffreihe".

*Primary Examiner*—Sreeni Padmanabhan
*Attorney, Agent, or Firm*—Blossom E. Loo

[57] ABSTRACT

A propene ether is selectively oxidized to an aldehyde-masked 2-hydroxypropanal using a metal-containing oxidation catalyst.

14 Claims, No Drawings

PROCESS FOR THE MANUFACTURE OF HYDROXYCARBONYL COMPOUNDS

This is the U.S. National Stage Application of PCT/EP97/02125 filed Apr. 23, 1997.

This invention relates to a process for the manufacture of a hydroxycarbonyl compound, more especially to the manufacture of lactic acid, 2-hydroxypropionic acid, and to a process for the manufacture of intermediates useful for syntheses of that and other compounds.

Lactic acid and its derivatives, especially salts and esters, have many industrial uses, primarily in the food industry but also increasingly in the manufacture of biodegradable polymers. Much of the product has long been obtained by fermentation of hexoses or hexose-producing raw materials, a procedure from which much unwanted by-product and effluent result; known synthetic methods have grown in commercial importance but they too present some environmental problems, and yields admit of improvement.

A synthetic route of present interest involves the selective oxidation of a propene ether in the presence of an aldehyde-group protecting or masking reagent to form 2-hydroxypropanal in which the aldehyde group is protected. This intermediate may then be deprotected and further oxidized to the desired lactic acid.

In Synthesis, August 1977, p 578, Frimer describes the preparation of an α-hydroxyacetal by epoxidation of an enol ether in an alcoholic solvent. The oxidizing agent used is m-chloroperbenzoic acid or $MoO_5HMPA$.

There remains a need, however, for a method of oxidation in which the oxidizing agent is more readily available or in which its conversion rate is high.

The present invention provides a process for the manufacture of a protected 2-hydroxy propanal in which a 1-propenyl ether is oxidized by hydrogen peroxide or an organic hydroperoxide in the presence of an aldehyde group-protecting reagent and a metal-containing oxidation catalyst.

The ether oxygen of the starting material, the propene ether, is advantageously linked to a hydrocarbyl, e.g., a saturated aliphatic or araliphatic, radical, advantageously a lower alkyl radical, e.g., one having at most four carbon atoms, preferably methyl, ethyl, or n-propyl. The radical may be substituted by non-hydrocarbyl groups, for example by a hydroxy group, as in, e.g., 2-hydroxyethyl, but is advantageously unsubstituted.

Reaction of the propene ether, to introduce a hydroxy group on the ethylenically bound carbon atom remote from the ether oxygen, is effected in the presence of an aldehyde group protecting reagent, a compound that forms a bond with the ethylenically bound carbon atom linked to the ether oxygen and provides a proton to the molecule. Such a protic masking or protecting compound may be, for example, an acid, especially a carboxylic acid, or, advantageously, an alcohol., in which case the resulting product is an a-hydroxy acetal, i.e., an acetal of 2-hydroxypropanal. The alcohol is advantageously an aliphatic alcohol, and may conveniently be an alcohol having a hydrocarbyl group corresponding to that of the ether starting material. It is advantageously a low-boiling alcohol, e.g., ethanol or methanol. The alcohol is advantageously present in at least a stoichiometric quantity, advantageously in a molar ratio to the propene ether of at least 5:1, preferably at least 10:1, and if desired up to 40:1. Ultimately, the reaction may be carried out in solution, in which case an excess of alcohol reactant may conveniently act as solvent.

As oxidizing agent, there may be mentioned, as indicated above, hydrogen peroxide, and an organic hydroperoxide, for example tert-butyl hydroperoxide (TBHP), ethylbenzene hydroperoxide, and cumene hydroperoxide. As oxidation catalyst is employed either a homogeneous or, preferably, a heterogeneous, catalyst. For example, there may be mentioned a metal oxide, for example $TiO_2$, deposited on an amorphous support, e.g., silica, or a metal aerogel or xerogel. A heteropolyanionic acid catalyst is also suitable, for example, a polyoxometallate of the general formula $XM_{12}O_{40}{}^{x-8}$ wherein M represents a metal ion, e.g., Mo(VI), W(V), or V(V), and X represents P(V) or Si(IV) and x represents the oxidation state of the atom X. (See Cat. Rev. Sci. Eng. (1995) 37(2), 311 to 352).

Another suitable catalyst is a tetranuclear manganese complex or a tetranuclear metal complex having a mixed metal core, as described in U.S. Pat. Nos. 5,025,101 and 5,504,266, the disclosures of which are incorporated herein by reference. Preferably, a transition metal oxide catalyst in a high oxidation state, e.g., Mo(VI), W(VI) Ti(IV), Cr(VI), Zr(IV), V(V), Os(VI), Se(IV), Re(VI, VI, and VII) and Ru(VI and VIII), or a metal-containing, especially a titanium-containing, molecular sieve, especially one in which at least part of the metal forms part of the structure of the molecular sieve is used. Most preferably, a Ti-silicalite, e.g., TiMCM-41, TS-1, TS-2, or a zeolite, e.g., Ti-β, is used. The use of a heterogeneous catalyst facilitates separation of the reaction product as well as catalyst regeneration when necessary. Advantageously, a catalyst concentration of 0.1 to 20 g per mole of propene ether is employed.

While the catalyst may be introduced in different molecular forms, it is believed that the active species is an oxide, or a complex oxide, of the metal (or metals) present. Preferred reaction conditions vary with the catalyst, and oxidant. A temperature in the range of 0° C. to 150° C., preferably 40° C. to 100° C., at reaction times of from 1 to 10 hours, may typically be used. If a continuous process is used, advantageously a weight hourly space velocity (WHSV) of 0.1 to 100, based on catalyst weight, is employed.

The resulting protected 2-hydroxypropanal may be hydrolysed, if desired in situ, by a number of different routes. For example, acid hydrolysis provides 2-hydroxypropanal, using a dilute mineral acid or an ion exchange resin or a molecular sieve in acid form. Hydrolysis using dilute sulphuric acid is described by A. Wohl, Berichte, 1908, 3599 at 3608, using 0.1 N sulphuric acid for 3 days at room temperature. Under hydrolysis conditions, isomerization of the initially formed 2-hydroxypropanal to hydroxyacetone, itself a useful intermediate, may take place. At a given temperature, overall conversion is enhanced as the mole ratio of water to hydroxyacetal is increased to about 20:1, as is the molar proportion of 2-hydroxypropanal formed. Advantageous molar ratios are in the range of 5:1 to 20:1. The proportion of hydroxyacetone formed increases with time.

The overall conversion increases with catalyst concentration, as does the selectivity to hydroxyacetone. If hydroxypropanal is the desired product, then moderate catalyst concentrations, e.g., up to 5 wt %, based on acetal, may be used whereas if the acetone is the desired product higher, e.g., up to 20 wt %, concentrations are appropriate.

Higher temperatures, e.g., up to 90° C., improve conversion and favour hydroxyacetone yield.

Advantageously, HZSM-5 or, preferably, H-β, is employed as catalyst.

2-hydroxypropanal may be oxidized, e.g., by molecular oxygen or air. The oxidation may be carried out in the presence of a catalyst, e.g., a supported metal (for example, palladium, platinum, ruthenium or nickel), catalyst.

Alternatively, the protected 2-hydroxypropanal may be hydrolysed and oxidized in a single step to lactic acid.

The propenyl ether required as starting material may be obtained by acetalization of propanal and decomposing the acetal, e.g., by elimination of one molecule of alcohol, propanal being conveniently obtained by hydroformylation of ethylene, including dilute ethylene.

The following Examples illustrate the invention:

EXAMPLE 1

5 g (0.16 mol) of methanol were mixed with 5 mmol $H_2O_2$ (30% in $H_2O$) and 20 mmol of 1-methoxypropene. 0.25 g of TS-1 were added, and the mixture heated at 40° C. for 2 hours. Analysis showed 98% conversion of $H_2O_2$ and 46% conversion of the methoxypropene, of which 54 mol % was to 2-hydroxy-1,1-dimethoxypropane and 46 mol % was to 1,1-dimethoxypropane.

EXAMPLE 2

5 g (0.16 mol) of methanol were mixed with 14 mmol of 1-methoxypropene and 14 mmol of TBHP (80% in di-tert butylperoxide). 0.1 g TiMCM-41 were added and the mixture heated at 100° C. for 1 hour. 99% of both the methoxypropene and the TBHP were converted; the molar selectivity was 56% to hydroxyacetal, 38% to 1,1-dimethoxypropane and 8% to 1-methoxy-1-perbutoxypropane.

EXAMPLE 3

10 g (0.3 mol) of methanol were mixed with 10 mmol of TBHP (80% in di-tert butyl peroxide) and 40 mmol of 1-methoxypropene. 1 mmol of $Mo(CO)_6$ was added, and the mixture heated at 50° C. for 3 hours. The conversion of TBHP was 100%, and that of 1-methoxypropene was 61.5%, of which the molar selectivity was 41.5% to a-hydroxyacetal and 58.5% to 1,1-dimethoxypropane. The conversion of the TBHP was 100%.

Hydrolysis of Hydroxyacetal and Oxidation to Lactic Acid—2 stage—Examples 4 to 10

(Hydrolysis: Examples 4 to 9, Oxidation: Example 10)

2 g of 2-hydroxy-1,1-dimethoxypropane were mixed with 20 g of water in the presence of an acid catatyst. In Example 4, the temperature was maintained at room temperature for 5 days, while in Examples 5 to 9 the reaction mixture was maintained at 60° C. for 5 hours. Table 1 below indicates the catalyst, catalyst strength, reaction and conversion in each case.

TABLE 1

| Example No. | Acid | $H^+$/Acetal (molar) | $H^+$ conc (mol/l) | Conv., % |
|---|---|---|---|---|
| 4 | $H_2SO_4$ | 1/33 | 0.05 | 100 |
| 5 | $H_2SO_4$ | 1/500 | 0.00075 | 100 |
| 6 | $H_2SO_4$ | 1/250 | 0.00150 | 99 |
| 7 | $H_2SO_4$ | 1/100 | 0.00375 | 100 |
| 8 | Amberlyst 15 | — | 4 g/l | 99 |
| 9 | Zeolite H-β | — | 50 g/l | 100 |

Amberlyst is a trade mark for an ion exchange resin.

Amberlyst is a trade mark for an ion exchange resin.

EXAMPLE 10

Hydroxypropanal was oxidized batchwise with oxygen at atmospheric pressure in a 50 ml flask equipped with a stirrer, condenser and port for gas inlet.

Hydroxypropanal solution (2 g in 20 ml water) and a 5% platinum on carbon catalyst (0.1 g) were loaded into the flask with stirring at 60° C. Oxygen was bubbled for 5 hours, the oxidation reaction starting immediately. Reaction rate and product distribution were measured by oxygen consumption, HPLC, and NMR. The results showed 44.4% conversion with a selectivity to lactic acid of 92.4%. The only by-product resulted from the further oxidation of lactic acid to pyruvic acid (7.6%).

Single stage Oxidative Hydrolysis of Hydroxyacetal to Lactic Acid

EXAMPLE 11

1.8 g of 2-hydroxy-1,1-dimethoxypropane were mixed with 10 g water, 0.2 g of a 5% platinum on carbon catalyst, and 0.1 g of an acidic ion exchange resin, Amberlyst 15, in a 30 ml flask equipped with stirrer, condenser, and gas inlet port. Oxygen at atmospheric pressure was passed through the reaction mixture for 21 hours at room temperature. Analysis showed 87 mole per cent of the hydroxyacetal was converted, with molar selectivity of 30% to lactic acid, 68% to hydroxypropanal, and 0.5% to pyruvic acid.

EXAMPLES 12 TO 25

Hydrolysis of Hydroxyacetal to 2-Hydroxypropanal and Hydroxyacetone

In these examples the effects of varying the reaction conditions on conversion and selectivities (given below in molar %) are observed. First, the effect of the molar ratio of water:substrate (hydroxyacetal) was investigated. The results are shown in Table 2, below.

TABLE 2

| | | Time, hours | | | | | | | | |
|---|---|---|---|---|---|---|---|---|---|---|
| Ex. No. | Molar ratio water:substrate | 1 | 3 | 5 | 1 | 3 | 5 | 1 | 3 | 5 |
| | | Conversion, % | | | OH-Propanal, % | | | OH-Acetone, % | | |
| 12 | 5:1 | 20 | 68 | 82 | 87 | 70 | 63 | 13 | 30 | 37 |
| 13 | 10:1 | 24 | 78 | 92 | 93 | 84 | 72 | 8 | 16 | 28 |
| 14 | 20:1 | 32 | 93 | 98 | 100 | 83 | 74 | 0 | 17 | 26 |
| 15 | 50:1 | 16 | 83 | 100 | 100 | 91 | 85 | 0 | 9 | 15 |

Reaction Conditions: Catalyst Concentration 5 wt %, H-β, Si:Al ratio 28:1. Temperature 70° C.

Second, the effect of varying the weight ratio of catalyst-:substrate was investigated. Results are shown in Table 3.

TABLE 3

| | | Time, hours | | | | | | | | |
|---|---|---|---|---|---|---|---|---|---|---|
| Ex. No. | Wt, %, catalyst to substrate | 1 | 3 | 5 | 1 | 3 | 5 | 1 | 3 | 5 |
| | | Conversion, % | | | OH-Propanal, % | | | OH-Acetone, % | | |
| 16 | 1 | 0 | 8 | 17 | — | 100 | 91 | — | 0 | 9 |
| 17 | 5 | 32 | 93 | 98 | 100 | 83 | 74 | 0 | 17 | 26 |
| 18 | 10 | 56 | 97 | 99 | 93 | 70 | 56 | 7 | 30 | 44 |
| 19 | 20 | 96 | 99 | 100 | 78 | 41 | 23 | 22 | 59 | 77 |

Reaction Conditions: Molar Ratio Water:Substrate 20:1, Catalyst as in Example 12, Temperature 70° C.

Next, the effect of temperature was investigated. Results are as shown in Table 4.

TABLE 4

| Ex. No. | Temperature, % | Conversion, % | | | OH-Propanal, % | | | OH-Acetone, % | | |
|---|---|---|---|---|---|---|---|---|---|---|
| | | 1 | 3 | 5 | 1 | 3 | 5 | 1 | 3 | 5 |
| 20 | 22 | 0 | 8 | 17 | — | 100 | 91 | — | 0 | 9 |
| 21 | 50 | 24 | 94 | 98 | 93 | 83 | 71 | 7 | 17 | 29 |
| 22 | 70 | 31 | 93 | 98 | 100 | 83 | 74 | 0 | 17 | 26 |
| 23 | 90 | 95 | 97 | 99 | 85 | 70 | 56 | 15 | 30 | 44 |

Conditions as in Example 17, but with variation of temperature.

The effect of changing the catalyst to ZSM-5, Si:Al ratio 30:1, under conditions similar to those of Example 23 was examined; the results are shown in Table 5.

TABLE 5

| Ex. No. | Catalyst | Conv, % | | OH-Propanal, % | | OH-Acetone, % | |
|---|---|---|---|---|---|---|---|
| | | 1 | 3 | 1 | 3 | 1 | 3 |
| 24 | H-β | 95 | 100 | 85 | 51 | 15 | 49 |
| 25 | ZSM-5 | 17 | 54 | 53 | 46 | 47 | 54 |

What is claimed is:

1. A process for the manufacture of 2-hydroxypropanal having a protected aldehyde group which comprises oxidizing a 1-propenyl ether by hydrogen peroxide or an organic hydroperoxide in the presence of an aldehyde group-protecting reagent and a metal-containing oxidation catalyst.

2. A process as claimed in claim 1, wherein the oxygen atom of the ether is linked to a saturated hydrocarbyl group.

3. A process as claimed in claim 1, wherein a hydroperoxide is used, and wherein the hydroperoxide is tert-butyl hydroperoxide.

4. A process as claimed in claim 1, wherein the protecting reagent is an alcohol.

5. A process as claimed in claim 1, wherein a heterogeneous catalyst is used.

6. A process as claimed in claim 1, wherein a titanium-containing molecular sieve is used.

7. A process as claimed in claim 1, wherein the resulting protected 2-hydroxypropanal is hydrolysed to 2-hydroxypropanal.

8. A process as claimed in claim 1, wherein the resulting protected 2-hydroxypropanal is hydrolysed and oxidized to lactic acid.

9. A process as claimed in claim 1, wherein the resulting protected 2-hydroxypropanal is hydrolysed and isomerized to hydroxyacetone.

10. A process as claimed in claim 1, wherein said aldehyde group-protecting reagent is protic.

11. A process as claimed in claim 1, wherein said aldehyde group-protecting reagent is selected from the group consisting of an alcohol, an acid and a combination thereof.

12. A process as claimed in claim 11, wherein said acid is a carboxylic acid.

13. A process as claimed in claim 1, wherein the oxygen atom of the ether is linked to a hydroxyhydrocarbyl group.

14. A process as claimed in claim 13, wherein said hydroxyhydrocarbyl group is 2-hydroxyethyl.

* * * * *